(12) United States Patent
DeLonzor et al.

(10) Patent No.: US 9,050,072 B2
(45) Date of Patent: *Jun. 9, 2015

(54) CRYOPROBE FOR LOW PRESSURE SYSTEMS

(71) Applicant: Sanarus Technologies, LLC, Pleasanton, CA (US)

(72) Inventors: Russell L. DeLonzor, San Ramon, CA (US); James B. Ross, Pleasanton, CA (US); Mathew J. Nalipinski, Pleasanton, CA (US); Keith Turner, Cambridge (GB); David J. Foster, Cambridge (GB); Tom A. Oakley, Cambridge (GB); Michael R. Cane, Cambridge (GB)

(73) Assignee: Sanarus Technologies, Inc., Pleasanton, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/095,188

(22) Filed: Dec. 3, 2013

(65) Prior Publication Data

US 2014/0163539 A1 Jun. 12, 2014

Related U.S. Application Data

(63) Continuation of application No. 12/942,347, filed on Nov. 9, 2010, now Pat. No. 8,597,285, which is a continuation of application No. 11/318,142, filed on Dec. 23, 2005, now abandoned.

(51) Int. Cl.
*A61B 18/18* (2006.01)
*A61B 18/02* (2006.01)
*A61B 18/00* (2006.01)

(52) U.S. Cl.
CPC ....... *A61B 18/02* (2013.01); *A61B 2018/00041* (2013.01); *A61B 2018/0268* (2013.01)

(58) Field of Classification Search
CPC ............... A61B 18/04; A61B 18/0218; A61B 2018/00005; A61B 2018/00011; A61B 2018/00035; A61B 2018/00041; A61B 2018/00047; A61B 2018/0212; A61B 2018/0262; A61B 2018/0281; A61B 2018/0287
USPC ..................................................... 606/20–26
See application file for complete search history.

(56) References Cited

U.S. PATENT DOCUMENTS 6,464,716 B1 * 10/2002 Dobak et al. .................. 607/105
6,706,037 B2 * 3/2004 Zvuloni et al. ................. 606/21

* cited by examiner

*Primary Examiner* — Joseph Stoklosa
*Assistant Examiner* — Amanda Scott
(74) *Attorney, Agent, or Firm* — K. David Crockett, Esq.; Niky Economy Syrengelas, Esq.; Crockett & Crockett, PC

(57) ABSTRACT

A cryoprobe for use in cryosurgery and other applications comprising a rigid outer tube, an inner coolant inlet tube, a short rigid penetrating segment extending distally from the distal end of the outer tube and a helical-shaped baffle having a heating element disposed about the outer surface of the inlet tube. The baffle is adapted to produce turbulent fluid flow improving heat transfer and is able to warm target tissue during rapid freezing and thawing cycles.

5 Claims, 4 Drawing Sheets

CRYOPROBE FOR LOW PRESSURE SYSTEMS

This application is a continuation of U.S. application Ser. No. 12/942,347 now U.S. Pat. No. 8,597,285 issued Dec. 3, 2013, which is a continuation of U.S. application Ser. No. 11/318,142, filed Dec. 23, 2005 now abandoned.

FIELD OF THE INVENTIONS

The inventions described below relate the field of cryoprobes and more specifically to cryoprobes used in surgical procedures.

BACKGROUND OF THE INVENTIONS

Cryosurgical probes are used to treat a variety of diseases. The cryosurgical probes quickly freeze diseased body tissue masses, causing the tissue to die after which it will be absorbed by the body, expelled by the body or sloughed off. Cryothermal treatment is currently used to treat prostate cancer and benign prostate disease, breast tumors and breast cancer, liver tumors and cancer, glaucoma and other eye diseases. Cryosurgery is also proposed for the treatment of a number of other diseases.

A variety of cryosurgical instruments, referred to as cryoprobes, cryosurgical ablation devices, and cryostats and cryocoolers, have been available for cryosurgery. The preferred device uses Joule-Thomson cooling in devices known as Joule-Thomson cryostats. These devices take advantage of the fact that most gases, when rapidly expanded, become extremely cold. In these devices, a high pressure gas such as gaseous argon or gaseous nitrogen is expanded through a nozzle inside a small cylindrical sheath made of steel, and the Joule-Thomson expansion cools the steel sheath to sub-freezing cryogenic temperature very rapidly.

Present cryoprobes utilizing Joule-Thomson systems have inherent disadvantages such as inefficient heat transfer, the possible occurrence of vapor lock and excessive use of cryogen. As a result, these systems require use of large quantities of gasses under high pressure and high flow rates, in part, to prevent vapor lock. Use of high-pressure gasses increases the overall costs of cryoprobes. This is due to the higher costs of materials required for use with systems utilizing high-pressure gases, the high cost associated with keeping source gases themselves at higher pressures and the large quantities of cryogen required for use with these systems. What is needed is a cryoprobe system requiring low pressure with low fluid volume and flow rates that avoids vapor lock and reduces the quantities of cryogen required by using cryogen more efficiently.

SUMMARY

The devices and methods described below provide for the cryo-ablation of a mass of targeted tissue. The devices include a probe with structures that permit the surgeon to secure and form an ice mass of a suspect mass or tumor. The probe is provided with a rigid tube and a sharp distal segment. To secure the tumor to the probe, the surgeon pierces the tumor with the distal segment. Inlet tubing extending within the rigid tube directs coolant to the distal tip to cool the tip. A helical-shaped baffle comprising a heating element is provided in the distal section of the cryoprobe to create turbulent fluid and improve heat transfer. Since the baffle comprises a heating element, it can be further used in rapid freezing and warming cycles directed at targeted tissue masses.

DETAILED DESCRIPTION OF THE INVENTIONS

Figure 1:
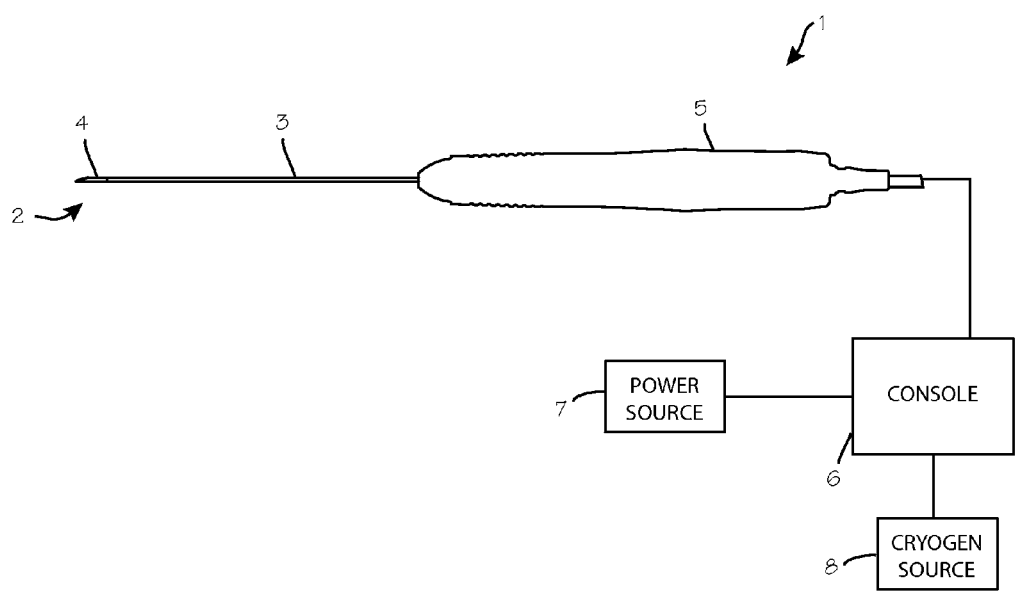
FIG. 1 illustrates a cryoprobe.

FIG. 1 illustrates a cryoprobe 1. The cryoprobe uses liquid nitrogen cooling to create a cooled region at the distal end 2. This cooled region adheres to a targeted lesion or tumor and creates an ice mass from the targeted tissue. The cryoprobe comprises a long, slender yet rigid outer tube 3. A short rigid penetrating segment 4 extends distally from the distal end of the rigid tube, and a suitable handle 5 is mounted on the proximal end of the tube. The handle is placed in fluid communication with a console 6 and the console is place in electrical communication with a power source 7 and fluid communication with a cryogen source 8. The console has a control system that is able to regulate use of power and the flow of cryogen to the cryoprobe.

Figure 2:
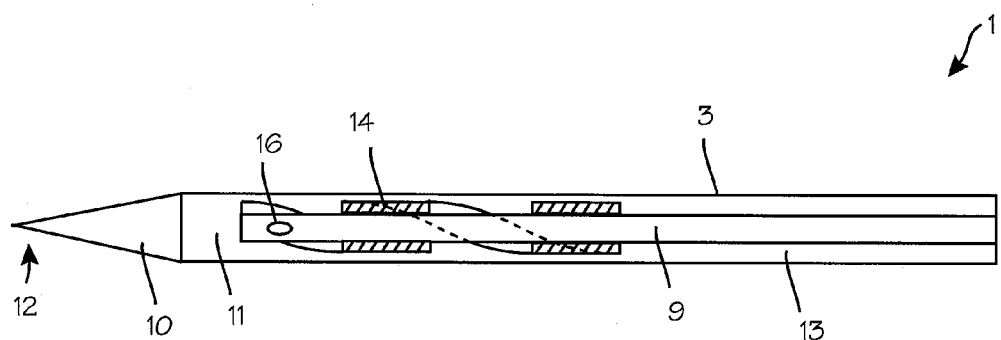
FIG. 2 shows a partial sectional side view of the distal end portion of the cryoprobe.
Figure 3:
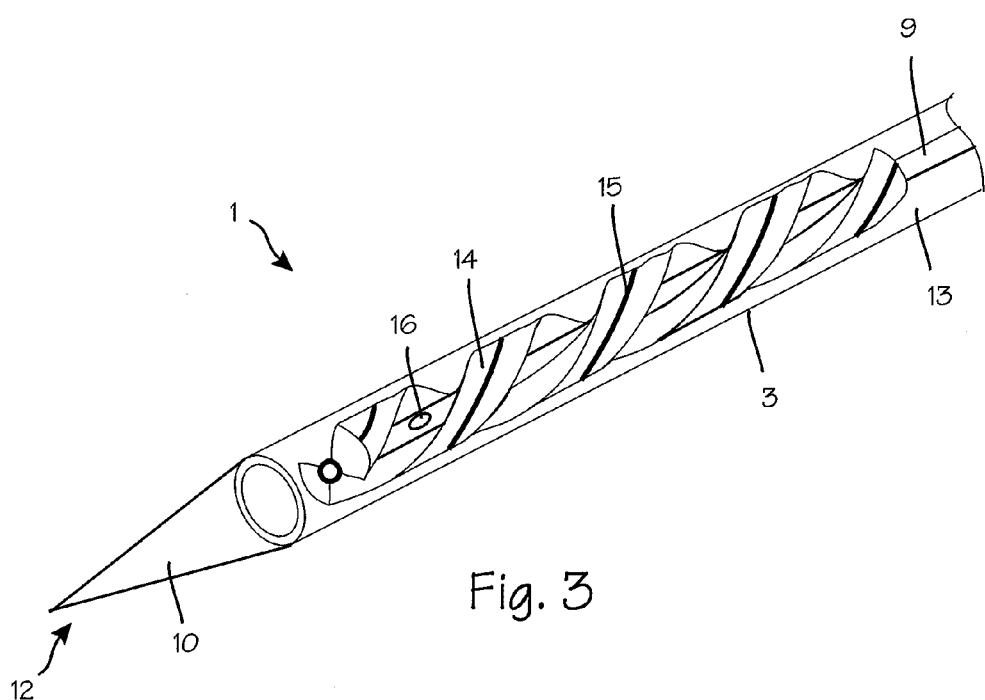
FIG. 3 shows a partial isometric sectional view of the distal end portion of the cryoprobe.

FIG. 2 shows a partial sectional side view of the distal end portion of the cryoprobe 1 while FIG. 3 shows a partial isometric sectional view of the distal end portion of the cryoprobe 1. The cryoprobe 1 comprises a rigid outer tube 3 and an inner coolant inlet tube 9. A short rigid penetrating segment 10 extends distally from the distal end of the outer tube 3. The coolant inlet 9 tube passes through the outer tube 3, extending to the distal end of the outer tube 3, terminating just proximal of the distal tip of the penetrating segment leaving a chamber 11 between the distal end of the inlet tube 9 and the proximal end of the penetrating element 4. The inlet tube may terminate by merely a straight cut or have a small nozzle of smaller internal diameter than the immediately upstream portion of the inlet tube. The outer tube 3 is made from stainless steel. However, the outer tube may also be manufactured from aluminum, brass, ceramics or MRI compatible materials. The inlet tube 9 is made from a polyetheretherketon (PEEK) or other lower thermally conductive material having a pressure and temperature capability sufficient for the pressures and temperatures anticipated for the particular application. Use of lower thermally conductive materials for the inlet tube 9 reduces the amount of cryogen required by the cryoprobe 1. Suitable inlet tube 9 material includes fluoropolymer tubing (FEP), Teflon®, polyimide and polyurethane.

The outer tube 3 has an outer diameter of about 2.7 mm, an internal diameter of about 2.4 mm, and a length of about 40 mm. The inlet tube 9 has an outer diameter of about 0.76 mm and an inner diameter of about 0.64 mm. These dimensions may vary depending on the materials used and the application for the cryoprobe. The penetrating segment 4 comprises a sharp distal tip 12. As can be seen from the cross section, the sharp distal tip is solid and adapted for piercing through a tumor. The length of the penetrating segment is chosen to be approximately the same size as the target tissue mass to be sampled. This penetrating segment is forced into a lesion or tumor. An annular cavity 13 or lumen is created by the outer surface of the inlet tube and the inner surface of the rigid outer tube 3. The liquid exiting the orifice of the inlet tube 9 counter-flows along the annular cavity and is exhausted from the probe to a suitable point far removed from the probe.

A helical-shaped baffle 14 comprising a heating element 15 is disposed about the outer surface of a distal portion of the inlet tube and extends proximally about 18 mm from the distal end of the inlet tube. However, the baffle 14 may extend up to about 40 mm proximal to the distal end of the inlet tube 9. The helical-shaped baffle is adapted to produce turbulent fluid flow in fluid flowing past the outer surface of the inlet tube. The baffle 14 improves heat transfer by creating turbulent flow and forcing the cryogen outward to come in contact with the inner diameter surface of the outer wall in the distal section of the cryoprobe. The baffle 14 can comprise a separate extrusion, a machined part or a preformed wire. The baffle 14 may be formed by winding the inlet tube 9 about the longitudinal axis or a second helical-shaped baffle may also be provided in the distal section of the probe.

The heating element 15 and the baffle 14 may be unitary and made from the same material or the heating element 15 may be separate from the baffle and made from a different material. When the heating element and baffle 14 are unitary the baffle 14 is manufactured from a material capable of being heated when placed in electrical communication with a power source. In FIG. 2, the baffle 14 is manufactured from nichrome wire placed in electrical communication with a power source. Thus, the baffle 14 provides both turbulent fluid flow while also able to function as a heating element. In FIG. 3, the baffle 14 is a helical structure machined from brass and the heating element 15 is a separate material disposed within the baffle. The temperature of the heating element is regulated by the console. A thermocouple 16 is disposed on the distal section of the cryoprobe 1 to measure temperatures at the probe tip.

Figure 4:
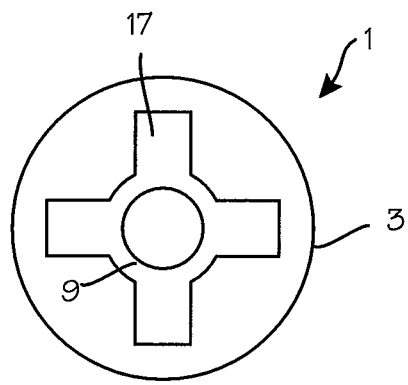
FIG. 4 illustrates a cryoprobe with a baffle having a cross-shaped cross-section disposed about the inlet tube.
Figure 5:
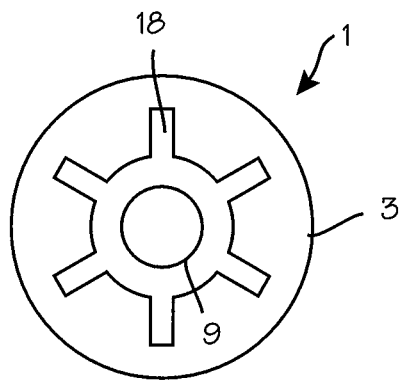
FIG. 5 illustrates a cryoprobe with a baffle having a sprocket cross-section disposed about the inlet tube.
Figure 6:
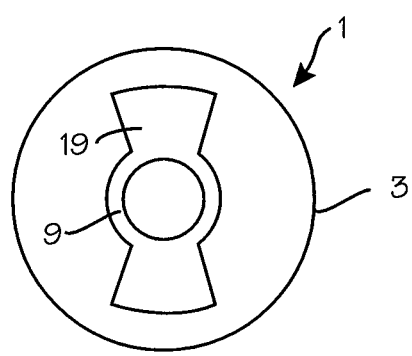
FIG. 6 illustrates a cryoprobe with a baffle having a cross-section with opposing arcuate trapezoidal sections disposed about an inlet tube.

FIGS. 4-6 illustrate cross-sections of various cryoprobes 1 having an outer tube 3 with baffles 14 comprising a heating element having differing configurations and disposed about the outer surface of the inlet tube. FIG. 4 illustrates a cryoprobe with a baffle having a cross-shaped 17 cross-section disposed about the inlet tube. FIG. 5 illustrates a cryoprobe with a baffle having a sprocket cross-section 18 disposed about the inlet tube. In FIG. 6, the baffle comprises a cross-section with opposing arcuate trapezoidal sections 19 disposed about the inlet tube. The baffles in FIGS. 4-6 improve heat transfer by creating turbulent flow while forcing the cryogen outward towards the inner diameter surface of the outer wall in the distal section of the cryoprobe where the non-target body tissue can further act as a heat sink.

Figure 7:
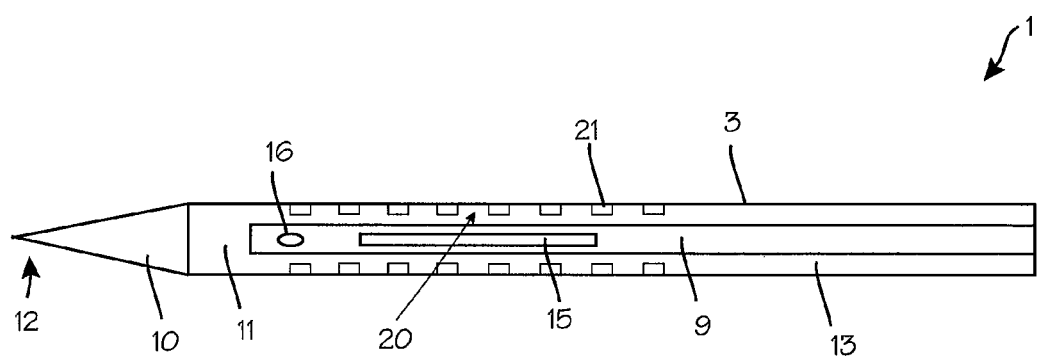
FIG. 7 depicts a cryoprobe having an outer tube with a grooved inner diameter.

FIG. 7 depicts a cryoprobe 1 having an outer tube 3 with a grooved inner diameter 20. The cryoprobe comprises an outer 3 tube and an inner coolant inlet tube 9. A short rigid penetrating segment 4 extends distally from the distal end of the outer tube. The coolant inlet tube passes through the outer tube, extending to the distal end of the outer tube, terminating just proximal to the distal tip of the penetrating segment 4 leaving a chamber between 11 the distal end of the inlet tube 9 and the proximal end of the penetrating element 4.

The inner diameter of the outer tube 3 is provided with helical-shaped groove 21 disposed about the inner surface of a distal portion of the outer tube. The grooves are adapted to produce turbulent fluid flow in fluid flowing past the inner surface of the outer tube. A heating element 15 such as nichrome wire in electrical communication with a power source is disposed in the distal section of the probe. The baffle 14 extends approximately 20 mm along the distal section of the inlet tube 9. A thermocouple is also disposed on the distal section of the cryoprobe to measure temperatures at the probe tip.

Figure 8:
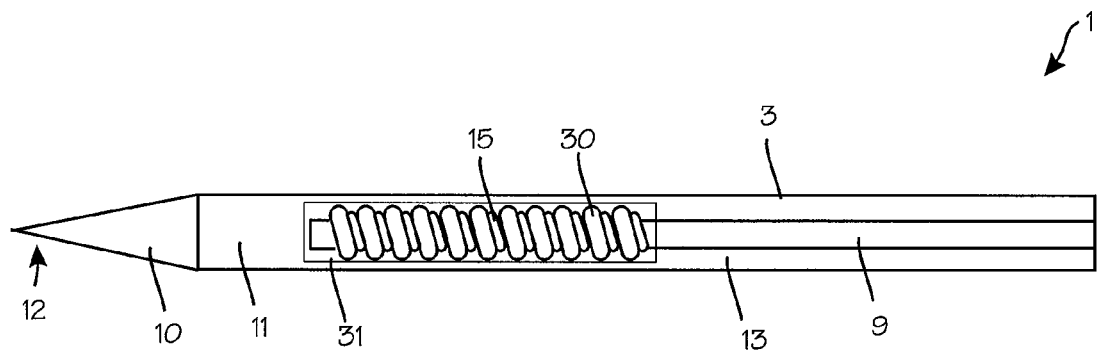
FIG. 8 illustrates a cryoprobe with a baffle comprising a tubular-shaped insulator and a heating element wound about the distal section of the inlet tube.

A cryoprobe 1 with a baffle 14 comprising a tubular-shaped insulator 30 and a heating element 15 wound about the distal section of the inlet tube 9 is illustrated in FIG. 8. The tubular insulator is manufactured from silicone while the heating element is manufactured from nichrome wire. This baffle and heating element configuration creates a tornado flow pattern in the exhaust cryogen. As the exhaust fluid flows past the baffle and heater wire, the pressure and inertia of the fluid creates a vortex while the exhaust fluid it forced towards the inner surface of the outer tube 3. A collar 31 having low electrical conductivity, but high thermal conductivity, may also be provided and disposed within the inner diameter of the outer tube to prevent electrical current from flowing from the heating element to the outer tube 3. In FIG. 8, the collar 31 is manufactured from a high purity, aluminum-nitride machinable ceramic with high strength and high thermal conductivity such as Shapal-M®.

When the cryoprobe 1 is in use, the inlet tube 9 is placed in fluid communication with a lightly pressurized liquid nitrogen source 8 by means of an inlet fitting. The pressures at the nitrogen source 8 can range from approximately 0.5 bar to about 30 bar. The liquid nitrogen at its source preferably has a source pressure of about 1.5 bar. The liquid nitrogen is supplied to the assembly through a pressure fitting, flows through a fluid supply line, flows through the inlet tube and exits the distal end of the inlet tube 9. The distal end of the inlet tube 9 is exposed to a cavity at the distal end of the outer tube 3 closed by the rigid penetrating segment 4. After expanding in the chamber, the fluid is at lower pressure and exhausts over the exhaust pathway which includes flow over outside of the inlet tube and the baffle. Typical pressure drops for the cryoprobe can be up to about 10% in the supply line, about 30% in the inlet tube and about 30% over the baffle 14. The liquid nitrogen cools the distal tip of the probe to temperatures as low as −196° C. when steady flow has been established. The liquid nitrogen cools the inner surface of the rigid penetrating segment 4, thereby cooling the outer surface of the segment. The outer surface of the penetrating segment 4 is placed against the targeted tissue to be cooled by the physician and the targeted tissue becomes an ice mass. Fluid flowing past the outer surface of the inlet tube is placed in contact with the helical-shaped baffle creating a turbulent helical flow path and forcing the cryogen towards the inner surface of the outer tube 3. Turbulent fluid flow provides for improved heat transfer between the cryoprobe and targeted tissue. As the liquid nitrogen boils, the exhaust gas flows through the remainder of the exhaust gas pathway which includes the flexible tube and the vent which vents the exhaust gas to atmosphere. Depending on the flow rates of the nitrogen, boiling can occur once the nitrogen flows past the baffle 14. In order to minimize cryogen consumption, flow rates can be reduced to a level where the nitrogen is about 90% vapor by the time it flows past the baffle 14. A second heating element may be disposed in the handle and placed in thermal communication with the exhaust gas, so the exhaust gas can be vented near room temperature at the handle and not vented at the console.

In many surgical applications, it is beneficial to have a means for warming the cryoprobe 1 quickly. This is desired for therapeutic and practical reasons. Current theory suggests that two cycles of rapid freezing and thawing provides better cryoablation than a single freeze. Practically, it can take a long time for the ice mass to thaw so that the cryoprobe can be withdrawn from the body. Unless natural thawing is medically indicated, natural thawing is a waste of time. Therefore, a means for heating the targeted tissue is also provided within the cryoprobe 1. Since the baffle 14 is constructed from nichrome heater wire, the baffle 14 may be quickly heated during cycles of rapid freezing and warming of the targeted tissue. Once the ice mass has been formed, the heating element can heat the distal end of the cryoprobe to temperatures ranging between about 20° C. to about 60° C. For optimal results, temperatures of about are used for fast removal of the cryoprobe 1 with minimizing risk of damage to tissue adjacent to the targeted tissue.

While the preferred embodiments of the devices and methods have been described in reference to the environment in which they were developed, they are merely illustrative of the principles of the inventions. Other embodiments and configurations may be devised without departing from the spirit of the inventions and the scope of the appended claims.

We claim:

1. A device comprising:
   a rigid outer tube having in inner surface;
   a coolant inlet tube disposed within the outer tube;
   a short rigid penetrating segment extending distally from a distal end of the outer tube;
   and a helical-shaped baffle having a heating element disposed about a distal outer surface of the inlet tube, said baffle disposed about a distal section of the inlet tube and terminating proximal of a distal tip of the penetrating segment and adapted to create turbulent fluid flow in fluid and force cryogen towards the inner surface of the outer rigid tube.

2. The device of claim 1 wherein the baffle and the heating element are unitary.

3. The device of claim 2 wherein the baffle comprises nichrome wire.

4. The device of claim 1 wherein the baffle comprises an extrusion, a machined part or a preformed wire.

5. A device comprising:
   a rigid outer tube having an inner diameter;
   a coolant inlet tube disposed within the outer tube;
   a short rigid penetrating segment extending distally from a distal end of the outer tube;
   a helical-shaped baffle disposed about a distal section of the inlet tube and terminating proximal of a distal tip of the penetrating segment; and
   a heating element disposed within the distal section of the outer tube.

\* \* \* \* \*